United States Patent

Stroech et al.

Patent Number: 4,938,791
Date of Patent: Jul. 3, 1990

[54] FUNGICIDAL AND PLANT GROWTH-REGULATING HYDROXYETHYL-AZOLYL DERIVATIVES

[75] Inventors: Klaus Stroech, Solingen; Klaus Böckmann, Wuppertal; Stefan Dutzmann, Duesseldorf; Wilhelm Brandes, Leichlingen; Klaus Lürssen, Bergisch-Gladbach; Paul Reinecke, Leverkusen, all of Fed. Rep. of Germany

[73] Assignee: Bayer Aktiengesellschaft, Leverkusen, Fed. Rep. of Germany

[21] Appl. No.: 211,799

[22] Filed: Jun. 24, 1988

[30] Foreign Application Priority Data

Jul. 1, 1987 [DE] Fed. Rep. of Germany ....... 3721696
Apr. 20, 1988 [DE] Fed. Rep. of Germany ....... 3813129

[51] Int. Cl.$^5$ ................. A01N 43/653; C07D 249/08
[52] U.S. Cl. ............................................ 71/92; 71/76; 548/101; 548/268.6; 514/184; 514/383
[58] Field of Search ............... 548/101, 262; 514/184, 514/383; 71/92, 76

[56] References Cited

U.S. PATENT DOCUMENTS 4,734,126  3/1988  Holmwood et al. .................... 71/76

FOREIGN PATENT DOCUMENTS 040345   11/1981  European Pat. Off. ............ 548/262
0040350  11/1981  European Pat. Off. .
061835   10/1982  European Pat. Off. ............ 548/262
0087148  8/1983   European Pat. Off. .
0180136  5/1986   European Pat. Off. .
0196038  10/1986  European Pat. Off. .
2129000  5/1984   United Kingdom ................ 548/262

Primary Examiner—Michael L. Raymond
Assistant Examiner—Patricia L. Morris
Attorney, Agent, or Firm—Sprung Horn Kramer & Woods

[57] ABSTRACT

Fungicidal and plant growth regulating hydroxyethylazolyl derivatives of the formula

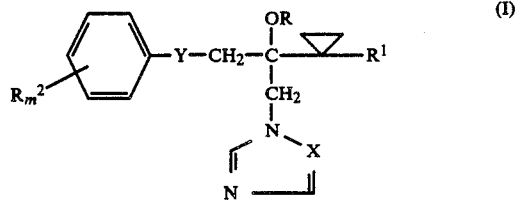

in which
R represents hydrogen, alkyl or acyl,
$R^1$ represents halogen, optionaly substituted phenyl or the grouping —Z—$R^3$, wherein
Z represents oxygen, sulphur, SO or $SO_2$ and
$R^3$ represents optionally substituted phenyl,
$R^2$ represents halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, halogenoalkylthio having 1 or 2 carbon atoms and 1 to 5 halogen atoms, alkoximinomethyl with 1 to 4 carbon atoms in the alkoxy group, phenyl which is optionally substituted by alkyl having 1 or 2 carbon atoms and/or halogen, or phenoxy, which is optionally substituted by alkyl having 1 or 2 carbon atoms and/or halogen,
m represents the number 0, 1, 2 or 3,
X represents nitrogen or a CH group and
Y represents oxygen, sulphur, SO or $SO_2$, and addition products thereof with acids and metal salts. Intermediates of the formulas

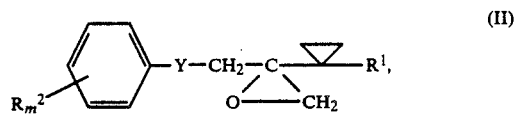

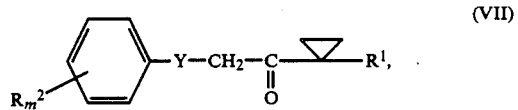

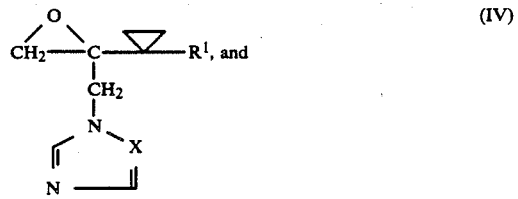

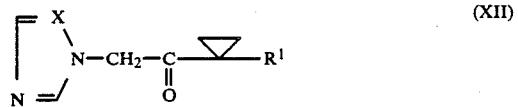

are also new.

9 Claims, No Drawings

FUNGICIDAL AND PLANT GROWTH-REGULATING HYDROXYETHYL-AZOLYL DERIVATIVES

The present invention relates to new hydroxyethylazolyl derivatives, several processes for their preparation and their use as fungicides and plant growth regulators.

It has already been disclosed that numerous hydroxyalkyl-azolyl derivatives possess fungicidal properties (compare EP-OS (European Published Specification) No. 0,040,345 and EP-OS (European Published Specification) No. 0,061,835). Thus, for example, 1-(4-chlorophenoxy)-2-cyclopropyl-1-(1,2,4-triazol-1-yl)-propan-2-ol can be employed for combating fungi. The activity of this substance is very good; however, the toleration by plants and the activity leave something to be desired in some cases.

New hydroxyethyl-azolyl derivatives of the formula

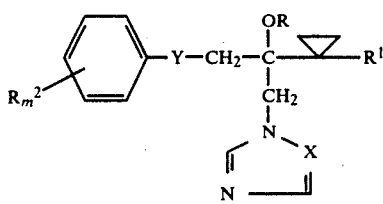   (I)

in which
R represents hydrogen, alkyl or acyl,
$R^1$ represents halogen, optionally substituted phenyl or the grouping —Z—$R^3$,
wherein
Z represents oxygen, sulphur, SO or $SO_2$ and
$R^3$ represents optionally substituted phenyl,
$R^2$ represents halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 halogen atoms, halogenoalkoxy having 1 or 2 carbon atoms and 1 to 5 halogen atoms, halogenoalkylthio having 1 or 2 carbon atoms and 1 to 5 halogen atoms, alkoximinomethyl with 1 to 4 carbon atoms in the alkoxy group, phenyl, which is optionally substituted by alkyl having 1 or 2 carbon atoms and/or halogen, or phenoxy, which is optionally substituted by alkyl having 1 or 2 carbon atoms and/or halogen,
m represents the numbers 0, 1, 2 or 3,
X represents nitrogen or a CH group and
Y represents oxygen, sulphur, SO or $SO_2$,
and their acid addition salts and metal salt complexes, have now been found.

Furthermore, it has been found that hydroxyethylazolyl derivatives of the formula (I) and their acid addition salts and metal salt complexes are obtained when
(a) oxiranes of the formula

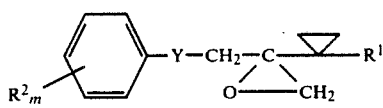   (II)

in which $R^1$, $R^2$, Y and m have the abovementioned meaning, are reacted with azoles of the formula

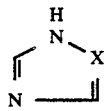   (III)

in which X has the abovementioned meaning, in the presence of an acid-binding agent and in the presence of a diluent, or
(b) azolyl derivatives of the formula

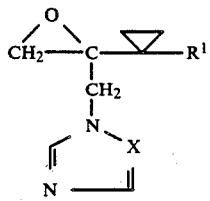   (IV)

in which
$R^1$ and X have the abovementioned meaning, are reacted with phenyl derivatives of the formula

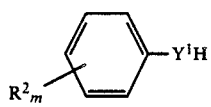   (V)

in which
$R^2$ and m have the abovementioned meaning and
$Y^1$ represents oxygen or sulphur,
in the presence of an acid-binding agent and in the presence of a diluent, or
(c) hydroxyethyl-azolyl derivatives of the formula

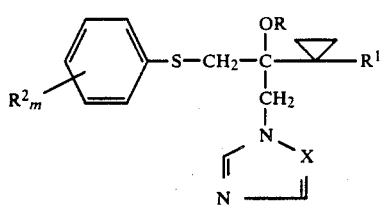   (Ia)

in which
R, $R^1$, $R^2$, X and m have the abovementioned meaning, are reacted with oxidants, if appropriate in the presence of a diluent, or
(d) hydroxyethyl-azolyl derivatives of the formula

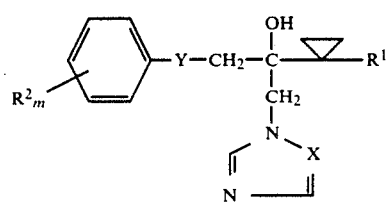   (Ib)

in which
$R^1$, $R^2$, X, Y and m have the abovementioned meaning, are reacted with strong bases in the presence of a diluent and the alcoholates of the formula

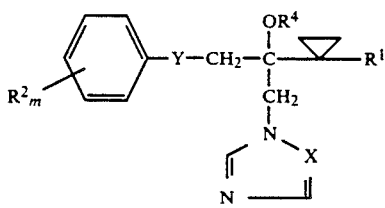

(Ic)

which

R$^1$, R$^2$, X, Y and m have the abovementioned meaning, and

R$^4$ represents a cationic radical of a base, produced in this reaction are reacted with halogen compounds of the formula $$R^5—Hal \quad (VI)$$

in which

R$^5$ represents alkyl or acyl and

Hal represents halogen, in the presence of a diluent, and subsequently, if desired, an acid or a metal salt is added to the compounds of the formula (I) thus obtained to form the acid addition salt or metal salt complex.

Finally, it has been found that the new hydroxyethyl-azolyl derivatives of the formula (I) and their acid addition salts and metal salt complexes possess strong fungicidal and plant growth-regulatory properties.

The substances according to the invention contain an asymmetrically substituted carbon atom. They can therefore occur in optically isomeric forms. The present invention relates both to the individual isomers and their mixtures.

Surprisingly, the substances according to the invention possess a better fungicidal and plant growth-regulatory activity than previously known compounds which resemble these most closely in terms of structure and with the same type of action.

Formula (I) provides a general definition of the hydroxyethyl-azolyl derivatives according to the invention. Preferably, in this formula R represents hydrogen, alkyl having 1 to 6 carbon atoms or alkylcarbonyl having 1 to 6 carbon atoms in the alkyl group, R$^1$ represents fluorine, chlorine, bromine, phenyl, which is optionally substituted by halogen, halogenoalkyl having 1 or 2 carbon atoms and 1 to 5 halogen atoms, alkyl having 1 to 4 carbon atoms and/or alkoxy having 1 to 4 carbon atoms, or the grouping —Z—R$^3$, wherein Z represents oxygen, sulphur, SO or SO$_2$ and R$^3$ represents phenyl, which is optionally substituted by halogen, halogenoalkyl having 1 or 2 carbon atoms and 1 to 5 halogen atoms, alkyl having 1 to 4 carbon atoms and/or alkoxy having 1 to 4 carbon atoms, R$^2$ represents fluorine, chlorine, bromine, methyl, ethyl, isopropyl, tert.-butyl, methoxy, methylthio, trifluoromethyl, trifluoromethoxy, trifluoromethylthio, methoximinomethyl, phenyl, which is optionally substituted by fluorine, chloride and/or methyl, or phenoxy, which is optionally substituted by fluorine, chlorine and/or methyl, m represents the numbers 0, 1, 2 or 3, X represents nitrogen or a CH group and Y represents oxygen, sulphur, SO or SO$_2$.

When m represents the numbers 2 or 3, the radicals representing R$^2$ can be identical or different.

Particularly preferred compounds are those of the formula (I) in which

R represents hydrogen, methyl, ethyl, n-propyl, isopropyl, n-butyl, isobutyl, methylcarbonyl, ethylcarbonyl, n-propylcarbonyl, isopropylcarbonyl, n-butylcarbonyl or isobutyl-carbonyl, R$^1$ represents fluorine, chlorine, bromine, phenyl, which is optionally monosubstituted to trisubstituted by identical or different substituents from the series comprising fluorine, chlorine, bromine, trifluoromethyl, methyl, ethyl, methoxy and/or ethoxy, or the grouping —Z—R$^3$, wherein Z represents oxygen, sulphur, SO or SO$_2$ and R$^3$ represents phenyl, which is optionally monoSubstituted to trisubstituted by identical or different substituents from the series comprising fluorine, chlorine, bromine, trifluoromethyl, methyl, ethyl, methoxy and/or ethoxy, R$^2$ represents fluorine, chlorine, bromine, methyl, ethyl, isopropyl, tert.-butyl, methoxy, methylthio, trifluoromethyl, triflporomethoxy, trifluoromethylthio, methoximinomethyl, phenyl, which is optionally substituted by fluorine, chlorine and/or methyl or phenoxy, which is optionally substituted by fluorine, chlorine and/or methyl, m represents the numbers 0, 1, 2 or 3, X represents nitrogen or a CH group and Y represents oxygen, sulphur, SO or SO$_2$.

Preferred compounds according to the invention are also addition products of acids and those hydroxyethyl-azolyl derivatives of the formula (I) in which R, R$^1$, R$^2$, X, Y and m have the meanings which have already been mentioned as preferable for these radicals or this index.

The acids which can be added to form acid addition products preferably include hydrohalic acids, such as, for example, hydrochloric acid and hydrobromic acid, in particular hydrochloric acid, and furthermore phosphoric acid, nitric acid, sulphuric acid, mono- and bifunctional carboxylic acid and hydroxycarboxylic acids, such as, for example, acetic acid, maleic acid, succinic acid, fumaric acid, tartaric acid, citric acid, salicylic acid, sorbic acid and lactic acid and also sulphonic acids, such as, for example, p-toluenesulphonic acid, 1,5-naphthalenedisulphonic acid or camphorsulphonic acid.

In addition, preferred compounds according to the invention are addition products of acids of metals of main groups II to IV and sub-groups I and II and also IV to VIII of the periodic table of the elements and those hydroxyethyl-azolyl derivatives of the formula (I) in which R, R$^1$, R$^2$, X, Y and m have the meanings which have already been mentioned as preferable for these radicals and this index.

The salts of copper, zinc, manganese, magnesium, tin, iron and nickel are particularly preferred here. Possible anions of these salts are those which are derived from those acids which result in physiologically acceptable addition products. In this connection, particularly preferred acids of this type are hydrohalic acids, such as, for example, hydrochloric acid and hydrobromic acid, and furthermore phosphoric acid, nitric acid and sulphuric acid.

The substances shown in the following table may be mentioned as examples of hydroxyethyl-azolyl derivatives of the formula (I).

TABLE 1

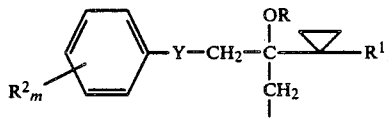

| $R^2_m$ | R | X | $R^1$ | Y |
|---|---|---|---|---|
| 2,4-Cl$_2$ | H | N | Cl | O |
| 2,4-F$_2$ | H | N | Cl | O |
| 4-CH$_3$ | H | N | Cl | O |
| 4-CF$_3$ | H | N | Cl | O |
| 4-OCF$_3$ | H | N | Cl | O |
| 4-OCH$_3$ | H | N | Cl | O |
| 4-SCH$_3$ | H | N | Cl | O |
| 2,4,6-Cl$_3$ | H | N | Cl | O |
| 4-Cl | H | N | F | O |
| 4-Cl | H | CH | Cl | O |
| 4-Cl | CH$_3$ | N | Cl | O |
| 4-Cl | H | N | –C$_6$H$_5$ | O |
| 4-Cl | H | N | –O–C$_6$H$_5$ | O |
| 4-Cl | H | N | –S–C$_6$H$_5$ | O |
| 4-Cl | H | N | –SO–C$_6$H$_5$ | O |
| 4-Cl | H | N | –SO$_2$–C$_6$H$_5$ | O |
| 4-C$_6$H$_5$ | H | N | Cl | O |
| 4-O-C$_6$H$_5$ | H | N | Cl | O |
| 4-t.-C$_4$H$_9$ | H | N | Cl | O |
| 2-Cl, 4-CH$_3$ | H | N | Cl | O |
| — | H | N | Cl | O |
| 4-Cl | –CO–CH$_3$ | N | Cl | O |
| 4-Cl | –C$_2$H$_5$ | N | Cl | O |
| 4-F | CH$_3$ | N | F | O |
| 2,4-Cl$_2$ | H | N | Cl | S |
| 2,4-F$_2$ | H | N | Cl | S |
| 4-CH$_3$ | H | N | Cl | S |
| 4-CF$_3$ | H | N | Cl | S |
| 4-OCF$_3$ | H | N | Cl | S |
| 4-OCH$_3$ | H | N | Cl | S |
| 4-SCH$_3$ | H | N | Cl | S |
| 2,4,6-Cl$_3$ | H | N | Cl | S |
| 4-Cl | H | N | F | S |
| 4-Cl | H | CH | Cl | S |
| 4-Cl | CH$_3$ | N | Cl | S |
| 4-Cl | H | N | –C$_6$H$_5$ | S |
| 4-Cl | H | N | –O–C$_6$H$_5$ | S |
| 4-Cl | H | N | –S–C$_6$H$_5$ | S |
| 4-Cl | H | N | –SO–C$_6$H$_5$ | S |
| 4-Cl | H | N | –SO$_2$–C$_6$H$_5$ | S |
| 4-C$_6$H$_5$ | H | N | Cl | S |
| 4-O-C$_6$H$_5$ | H | N | Cl | S |
| 4-t.-C$_4$H$_9$ | H | N | Cl | S |
| 2-Cl, 4-CH$_3$ | H | N | Cl | S |
| — | H | N | Cl | S |
| 4-Cl | –CO–CH$_3$ | N | Cl | S |
| 4-Cl | –C$_2$H$_5$ | N | Cl | S |
| 4-F | CH$_3$ | N | F | S |
| 2,4-Cl$_2$ | H | N | Cl | SO |
| 2,4-F$_2$ | H | N | Cl | SO |
| 4-CH$_3$ | H | N | Cl | SO |
| 4-CF$_3$ | H | N | Cl | SO |
| 4-OCF$_3$ | H | N | Cl | SO |
| 4-OCH$_3$ | H | N | Cl | SO |
| 2,4,6-Cl$_3$ | H | N | Cl | SO |
| 4-Cl | H | N | F | SO |
| 4-Cl | H | CH | Cl | SO |
| 4-Cl | CH$_3$ | N | Cl | SO |
| 4-Cl | H | N | –C$_6$H$_5$ | SO |

TABLE 1-continued (I)

Structure: $R^2_m$-phenyl-Y-CH$_2$-C(OR)(cyclopropyl-R$^1$)-CH$_2$-N(triazole)

| $R^2_m$ | R | X | R$^1$ | Y |
|---|---|---|---|---|
| 4-Cl | H | N | —O—phenyl | SO |
| 4-Cl | H | N | —SO—phenyl | SO |
| 4-phenyl | H | N | Cl | SO |
| 4-O-phenyl | H | N | Cl | SO |
| 4-t.-C$_4$H$_9$ | H | N | Cl | SO |
| 2-Cl, 4-CH$_3$ | H | N | Cl | SO |
| — | H | N | Cl | SO |
| 4-Cl | —CO—CH$_3$ | N | Cl | SO |
| 4-Cl | —C$_2$H$_5$ | N | Cl | SO |
| 4-F | CH$_3$ | N | F | SO |
| 2,4-Cl$_2$ | H | N | Cl | SO$_2$ |
| 2,4-F$_2$ | H | N | Cl | SO$_2$ |
| 4-CH$_3$ | H | N | Cl | SO$_2$ |
| 4-CF$_3$ | H | N | Cl | SO$_2$ |
| 4-OCF$_3$ | H | N | Cl | SO$_2$ |
| 4-OCH$_3$ | H | N | Cl | SO$_2$ |
| 2,4,6-Cl$_3$ | H | N | Cl | SO$_2$ |
| 4-Cl | H | N | F | SO$_2$ |
| 4-Cl | H | CH | Cl | SO$_2$ |
| 4-Cl | CH$_3$ | N | Cl | SO$_2$ |
| 4-Cl | H | N | phenyl | SO$_2$ |
| 4-Cl | H | N | —O—phenyl | SO$_2$ |
| 4-Cl | H | N | —SO$_2$—phenyl | SO$_2$ |
| 4-phenyl | H | N | Cl | SO$_2$ |
| 4-O-phenyl | H | N | Cl | SO$_2$ |
| 4-t.-C$_4$H$_9$ | H | N | Cl | SO$_2$ |
| 2-Cl, 4-CH$_3$ | H | N | Cl | SO$_2$ |
| — | H | N | Cl | SO$_2$ |
| 4-Cl | —CO—CH$_3$ | N | Cl | SO$_2$ |
| 4-Cl | —C$_2$H$_5$ | N | Cl | SO$_2$ |
| 4-F | CH$_3$ | N | F | SO$_2$ |

If 2-(1-chloro-cyclopropyl)-2-(4-chlorophenoxymethyl)-oxirane and 1,2,4-triazole are used as starting materials, then the course of process (a) according to the invention can be illustrated by the following equation:

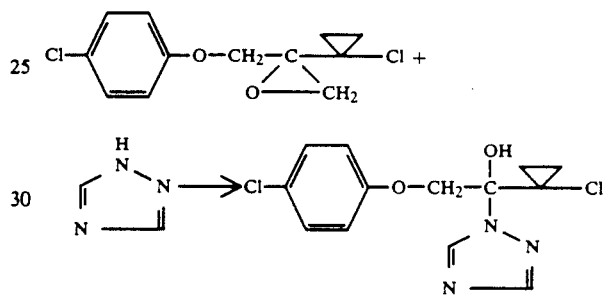

If 2-[1-(2-chlorophenoxy)-cyclopropyl]-2-[(1,2,4-triazol-1-yl)-methyl]-oxirane and 4-chloro-thiophenol are use as starting materials, then the course of process (b) according to the invention can be illustrated by the following equation:

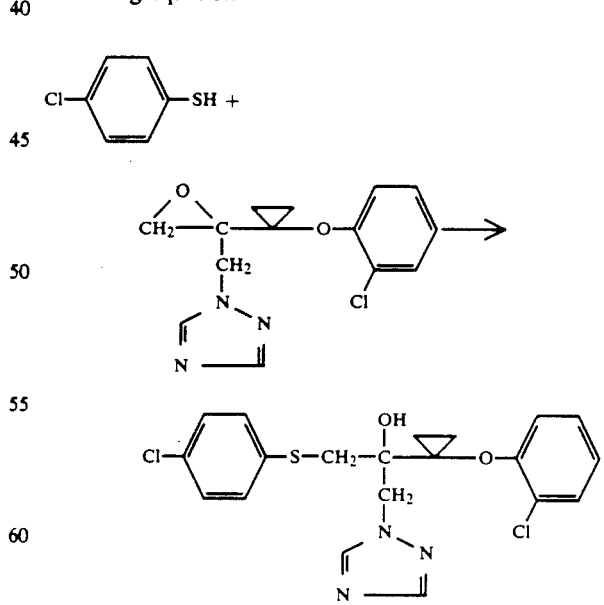

If 1-(4-chlorophenylmercapto)-2-[1-(2-chlorophenoxy)-cyclopropyl]-3-(1,2,4-triazol-1-yl)-propan-2-ol is used as starting material and aqueous hydrogen peroxide in glacial acetic acid as oxidant, then the course of process (c) according to the invention can be illustrated by the following: equation

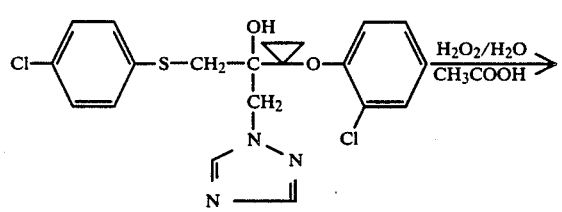

If 2-(1-chlorocyclopropyl)-1-(4-chlorophenoxyl)-3-(1,2,4-triazol-1-yl)propan-2-ol and sodium hydride are used as starting materials and iodomethane is used as a reaction component, then the course of process (d) according to the invention can be illustrated by the following equation:

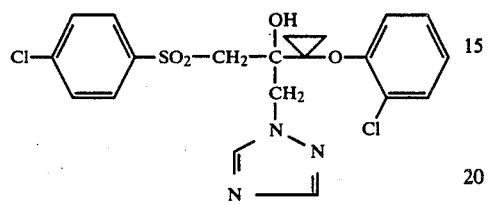

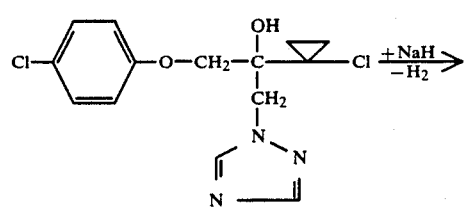

Formula (II) provides a general definition of the oxiranes required as starting materials for process (a) according to the invention. In this formula, $R^1$, $R^2$, Y and m preferably have those meanings which have already been mentioned as preferable for these radicals and for this index in connection with the description of the substances of the formula (I) according to the invention.

The oxiranes of the formula (II) were hitherto unknown. They can be prepared by reacting
(e) cyclopropylketones of the formula

in which
$R^1$, $R^2$, Y and m have the abovementioned meaning, either
(α) with dimethyloxosulphonium methylide of the formula $$(CH_3)_2\overset{\oplus}{S}O\overset{\ominus}{C}H_2 \quad \text{(VIII)}$$

or
(β) with dimethylsulphonium methylide of the formula $$(CH_3)_2\overset{\oplus}{S}\ \overset{\ominus}{C}H_2 \quad \text{(IX)}$$

in the presence of a diluent.

The cyclopropyl ketones of the formula (VII) required as starting materials in process (e) were hitherto also unknown. They can be prepared by reacting
(f) halogenoketones of the formula

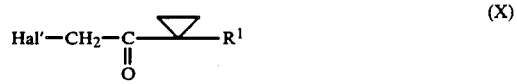

in which
$R^1$ has the abovementioned meaning and
Hal' represents chlorine or bromine,
with phenyl derivatives of the formula

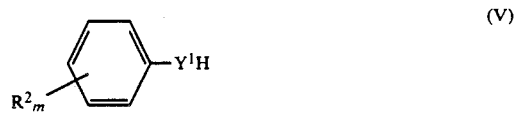

in which
$R^2$, $Y^1$ and m have the abovementioned meaning, in the presence of an acid-binding agent and if appropriate in the presence of a diluent, and if appropriate by then oxidizing the product.

Some of the halogenoketones of the formula (X) required as starting materials in process (f) are known. They can be prepared by reacting
(g) ketones of the formula

in which
$R^1$ has the abovementioned meaning, with chlorinating agents or brominating agents in the presence of a diluent.

The ketones of the formula (XI) required as starting materials for process (g) are known or can be synthesized by processes which are known in principle (compare Synthesis 1977, 189).

Possible chlorinating agents and brominating agents for process (g) are all chlorinating and brominating reagents customary for such reactions. Sulphuryl chloride, sulphuryl bromide, chlorine and bromine are preferably utilizable.

Suitable diluents for process (g) are all inert organic solvents customary for such reactions. Halogenated aliphatic hydrocarbons, such as methylene chloride, chloroform and carbon tetrachloride are preferably utilizable.

The reaction temperatures can be varied within a certain range in process (g). In general, the reaction is carried out at temperatures between $-10°$ C. and $+60°$ C., preferably between $0°$ C. and $+40°$ C.

When carrying out process (g), the reaction is generally carried out at atmospheric pressure as in the other processes described in this application. However, it is also possible to work at elevated or reduced pressure in each case.

When carrying out process (g), a stoichiometric amount or even a slight excess of chlorinating or brominating agent is generally employed per mol of ketone of the formula (XI). Working up takes place by customary methods. In general, a procedure is used in which the reaction mixture is successively washed with dilute aqueous sodium hydrogen carbonate solution and water, then dried and concentrated.

Formula (V) provides a general definition of the phenyl derivatives required as reaction components in process (f). In this formula, $R^2$, $Y^1$ and m preferably have those meanings which have already been mentioned as preferable for these radicals and for this index in connection with the description of the substances of the formula (I) according to the invention. The phenyl derivatives of the formula (V) are generally known compounds of organic chemistry.

For carrying out process (f), possible acid binding agents are all customary acid acceptors. Alkali metal carbonates and hydrogen carbonates, such as sodium carbonate, potassium carbonate or sodium hydrogen carbonate, and furthermore hydroxides and alcoholates of alkali metals, such as sodium hydroxide, potassium hydroxide, sodium methylate or potassium tert.-butylate, and in addition tertiary aliphatic or aromatic amines, such as triethylamine, N,N-dimethyl-cyclohexyl-amine, N,N-dimethyl-benzylamine and pyridine, and in addition cyclic amines, such as 1,5-diaza-bicyclo[4.3.0]non-5-ene (DBN), 1,8-diaza-bicyclo[5.4.0]undec-7-ene (DBU) and 1,4-diazabicyclo[2.2.2]octane (DABCO) are preferably utilizable.

For carrying out process (f), possible diluents are all inert organic solvents. Aliphatic and aromatic, optionally halogenated hydrocarbons such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as dimethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile and pyridine, and also strongly polar solvents, such as dimethylformamide and dimethyl sulphoxide are preferably utilizable.

The reaction temperatures can be varied within a relatively wide range in process (f). In general, the reaction is carried out at temperatures between $0°$ C. and $150°$ C., preferably between $20°$ C. and $130°$ C.

When carrying out process (f), 1 to 1.5 mols of phenyl derivative of the formula (V) and also 1 to 2 mols of acid-binding agent are generally employed per mol of halogenoketone of the formula (X). Working up takes place by customary methods. In general, a procedure is used in which the reaction mixture is concentrated after previously filtering off precipitated salts, if necessary, the residue is taken up in an organic solvent which is hardly miscible with water, and the resulting solution is washed, dried and then concentrated.

The dimethyl-oxo-sulphonium methylide of the formula (VIII) required as reaction component in process (e) is known (compare J. Am. Chem. Soc. 87, 1363–1364 (1965)). It is used in the above reaction in the freshly prepared state, by preparing it in situ by reaction of trimethyloxosulphonium iodide with sodium hydride or sodium amide, potassium tert.-butylate or sodium methylate, in the presence of a diluent.

The dimethylsulphonium methylide of the formula (IX) additionally possible as reaction component in process (e) is also known (compare Heterocycles 8,397 (1977)). It is also employed in the above reaction in the freshly prepared state, by preparing it in situ, for example, from trimethylsulphonium halide or trimethylsulphonium methylsulphate, in the presence of a strong base, such as, for example, sodium hydride, sodium amide, sodium methylate, potassium tert.-butylate or potassium hydroxide, in the presence of a diluent, such as tert.-butanol or dimethyl sulphoxide.

When carrying out process (e) suitable diluents are inert organic solvents. Alcohols, such as tert.-butanol, ethers, such as tetrahydrofuran or dioxane, and furthermore aliphatic and aromatic hydrocarbons, such as benzene, toluene or xylene, and also strongly polar solvents, such as dimethyl sulphoxide or acetonitrile are preferably utilizable.

The reaction temperatures can be varied within a relatively wide range when carrying out process (e). In general, the reaction is carried out between $0°$ C. and $100°$ C., preferably between $10°$ C. and $60°$ C.

When carrying out process (e), 1 to 3 mols of dimethyloxosulphonium methylide of the formula (VIII) or dimethylsulphonium methylide of the formula (IX) are generally employed per mol of cyclopropyl ketone of the formula (VII). The isolation of the oxiranes of the formula (II) takes place by customary methods.

When carrying out process (a) according to the invention, suitable acid-binding agents are all customary acid acceptors. All those acid-binding agents which have already been mentioned as preferable in connection with the description of process (f) are preferably utilizable.

When carrying out process (a) according to the invention, possible diluents are all customary inert organic solvents.

Nitriles, such as in particular acetonitrile; aromatic hydrocarbons, such as benzene, toluene and dichlorobenzene; formamides, such as in particular dimethylformamide, and also hexamethylphosphoric triamide are preferably utilizable.

The reaction temperatures can be varied within a relatively wide range when carrying out process (a) according to the invention. In general, the reaction is carried out at temperatures between $0°$ C. and $200°$ C., preferably between $50°$ C. and $150°$ C.

When carrying out process (a) according to the invention, 1 to 4 mols of azole of the formula (III) and 1 to 2 mols of base are preferably employed per mol of oxirane of the formula (II). The isolation of the final products takes place in a customary manner.

Formula (IV) provides a general definition of the azolyl derivatives required as starting materials for carrying out process (b) according to the invention. In this formula, $R^1$ and X preferably have those meanings which have already been mentioned as preferable for these radicals in connection with the description of the substances of the formula (I) according to the invention.

The azolyl derivatives of the formula (IV) were hitherto unknown. They can be prepared by reacting (h) azolylketones of the formula

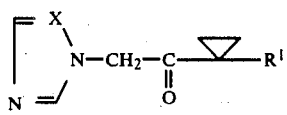
(XII)

in which
$R^1$ and X have the abovementioned meaning, either
(α) with dimethyloxosulphonium methylide of the formula

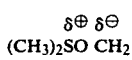
(VIII)

or
(β) with dimethylsulphonium methylide of the formula

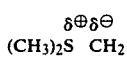
(IX)

in the presence of a diluent.

The azolylketones required as starting materials for carrying out process (h) were hitherto also unknown. They can be prepared by reacting
(i) halogenoketones of the formula

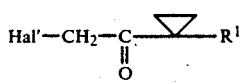
(X)

in which
$R^1$ has the abovementioned meaning and
Hal' represents chlorine or bromine, with azoles of the formula

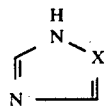
(III)

in which
X has the abovementioned meaning, in the presence of an acid-binding agent and in the presence of a diluent.

When carrying out process (i), the reaction conditions correspond to those of process (f).

Process (h) is carried out analogously to process (e).

The phenyl derivatives required as reaction components when carrying out process (b) according to the invention have already been discussed in connection with the description of process (f).

When carrying out process (b) according to the invention, all customary acid-binding agents and diluents can be employed. Those acid-binding agents and solvents which have already been mentioned as preferable in connection with the description of process (a) are preferably utilizable.

The reaction temperatures can also be varied within a relatively wide range when carrying out process (b) according to the invention. In general, the reaction is carried out at temperatures between 0° and 200° C., preferably between 50° and 150° C.

When carrying out process (b) according to the invention, an equivalent amount or even an excess of phenyl derivative of the formula (V) and 2 to 4 mols of acid-binding agent are generally employed per mol of azolyl derivative of the formula (IV). Working up takes place by customary methods. In general, a procedure is used in which the reaction mixture is filtered, the filtrate is concentrated by stripping off the diluent and the remaining residue is purified in a customary manner.

The hydroxyethyl-azolyl derivatives of the formula (Ia) required as starting materials for process (c) according to the invention are compounds according to the invention.

Possible reaction components in process (c) according to the invention are all oxidants customary for reactions of this type. Hydrogen peroxide and peracids, such as m-chloroperbenzoic acid and peracetic acid, are preferably utilizable.

When carrying out process (c) according to the invention, about 1 to 5 mols of oxidant are employed per mol of compounds of the formula (Ia) according to the invention. When 1 mol of oxidant, such as m-chloroperbenzoic acid in methylene chloride or hydrogen peroxide in acetic acid or acetic anhydride at temperatures between $-30°$ C. to $+90°$ C. is used, the compounds of the formula (I) according to the invention in which Y represents a —SO— grouping preferably result. Using excess oxidant and temperatures between 10° C. and 90° C. the compounds of the formula (I) according to the invention in which Y represents an —$SO^2$— grouping preferably result. The isolation of the oxidation products takes place in a customary manner.

The hydroxyethyl-azolyl derivatives of the formula (Ib) required as starting materials for process (d) according to the invention are also compounds according to the invention. Their conversion into the corresponding alcoholates takes place in a generally known manner, by reacting with suitable strong bases, such as amides or hydrides of alkali metals, quaternary ammonium hydroxides or phosphonium hydroxides in an inert diluent, such as, for example, dioxane, at room temperature. Accordingly, $R^3$ in the compounds of the formula (Ic) preferably represents an alkali metal cation, such as a sodium or potassium cation, or a quaternary ammonium or phosphonium cation.

Formula (VI) provides a general definition of the halogen compounds additionally required as starting materials in process (d) according to the invention. In this formula, $R^5$ preferably represents the meanings which have already been mentioned for the substituents $R^1$ in connection with the description of the substances of the formula (I) according to the invention, with the exception of the meaning of hydrogen. Hal preferably represents chlorine or bromine.

The halogen compounds of the formula (VI) are known or can be prepared by methods which are known in principle.

When carrying out process (d) according to the invention, suitable diluents are inert organic solvents. These preferably include ethers, such as diethyl ether or dioxane; aromatic hydrocarbons, such as benzene; and in individual cases also chlorinated hydrocarbons, such as chloroform, methylene chloride or carbon tetrachloride; and also hexamethylphosphoric triamide.

The reaction temperatures can be varied within a relatively wide range when carrying out process (d) according to the invention. In general, the reaction is carried out between 0° C. and 120° C., preferably between 20° C. and 100° C.

When carrying out process (d) according to the invention, hydroxyl compounds of the formula (Ib) are initially converted to the corresponding alcoholates of the formula (Ic) using strong bases. In the step which then follows, 1 to 2 mols of halogen compound of the formula (VI) are preferably employed per mol of an alcoholate of the formula (Ic).

For the isolation of the final products, the reaction mixture is freed of solvent, and water and an organic solvent are added to the residue. The organic phase is separated off, worked up in a customary manner and purified.

In a preferred embodiment, a procedure is expediently used which commences with a hydroxyl compound of the formula (Ib), the latter being converted into the alkali metal alcoholate by means of alkali metal hydride or alkali metal amide in a suitable organic solvent and the alkali metal alcoholate being reacted immediately without isolation with a halogen compound of the formula (VI), by means of which the compounds of the formula (I) according to the invention are obtained in one operation with the elimination of alkali metal halide.

According to a further preferred embodiment, the preparation of the alcohols and the reaction with a halogen compound of the formula (VI) are expediently carried out in a two-phase system, such as, for example, aqueous sodium hydroxide solution or potassium hydroxide solution/toluene or methylene chloride, with the addition of 0.01–1 mol of a phase-transfer catalyst, such as, for example, ammonium or phosphonium compounds, the alcoholates being reacted in the organic phase or on the boundary surface with the halides present in the organic phase.

The hydroxyethyl-azolyl derivatives of the formula (I) obtainable by the processes according to the invention can be converted into acid addition salts or metal salt complexes.

For the preparation of acid addition salts of the compounds of the formula (I), suitable acids are preferably those which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and can be isolated in a known manner, for example by filtering off, and can be purified by washing with an inert organic solvent, if necessary.

For the preparation of metal salt complexes of the compounds of the formula (I), suitable salts of metals are preferably those which have already been mentioned as preferred metal salts in connection with the description of the metal salt complexes according to the invention.

The metal salt complexes of the compounds of the formula (I) can be obtained in a simple manner by customary processes, thus, for example, by dissolving the metal salt in alcohol, for example ethanol and adding to compounds of the formula (I). Metal salt complexes can be isolated in a known manner, for example by filtering off, and can be purified by recrystallization, if necessary.

The active compounds according to the invention exhibit a strong microbicidal action and can be employed as fungicides.

Fungicides in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae;* Pseudomonas species, such as *Pseudomonas lachrymans;* Erwinia species, such as *Erwinia amylovora;* Pythium species, such as *Pythium ultimum;* Phytophthora species, such as *Phytophthora infestans;* Pseudoperonospora species, such as *Pseudoperonospora humuli* or *Pseudoperonospora cubense;* Plasmopara species, such as *Plasmopara viticola;* Peronospora species, such as *Peronospora pisi* or *P. brassicae;* Erysiphe species, such as *Erysiphe graminis;* Sphaerotheca species, such as *Sphaerotheca fuliginea;* Podosphaera species, such as *Podosphaera leucotricha;* Venturia species, such as *Venturia inaequalis;* Pyrenophora species, such as *Pyrenophora teres* or *P. graminea;* (conidia form: Drechslera, syn: Helminthosporium); Cochliobolus species, such as *Cochliobolus sativus;* (conidia form: Drechslera, syn: Helminthosporium); Uromyces species, such as *Uromyces appendiculatus;* Puccinia species, such as *Puccinia recondita;* Tilletia species, such as *Tilletia caries;* Ustilago species, such as *Ustilago nuda* or *Ustilago avenae;* Pellicularia species, such as *Pellicularia sasakii;* Pyricularia species, such as *Pyricularia oryzae;* Fusarium species, such as *Fusarium culmorum;* Botrytis species, such as *Botrytis cinerea;* Septoria species, such as *Septoria nodorum;* Leptosphaeria species, such as *Leptosphaeria nodorum;* Cercospora species, such as *Cercospora canescens;* Alternaria species, such as *Alternaria brassicae* and Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are suitable in particular for combating cereal and rice diseases, such as rust, mildew, *Cochliobolus sativus, Pyrenophora teres* and *Leptosphaeria nodorum* in cereals, or *Pyricularia oryzae* in rice. They can furthermore be used against Sphaerotheca in cucumbers.

In addition, the active compounds according to the invention also possess plant growth regulatory properties.

The active compounds according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth-regulating substances can be employed, for example, to inhibit vegetative growth of the plants. Such inhibition of growth is, inter alia, of economic interest in the case of grasses, since it is thereby possible to reduce the frequency of cutting the grass in ornamental gardens, parks and sports grounds, at road verges, at airports or in fruit orchards. The inhibition of growth of herbaceous and woody plants at road verges and in the vicinity of pipelines or overland lines or, quite generally, in areas in which heavy additional growth of plants is undesired, is also of importance.

The use of growth regulators to inhibit the growth in length of cereals is also important. The danger of bending ("lodging") of the plants before harvesting is thereby reduced or completely eliminated. Furthermore, growth regulators can strengthen the stem of cereals, which again counteracts lodging. Use of growth regulators for shortening and strengthening the stem enables higher amounts of fertilizer to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beets, sugar cane, pineapples and citrus fruit or to increase the protein content in soy beans or cereals. Using growth regulators it is also possible, for example, to inhibit the degradation of desired constituents, such as, for example, sugar in sugar beets or sugar cane, before or after harvesting. It is also possible favorably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the one hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a desired degree ("thinning out") in order to interrupt the alternance. By alternance there is understood the peculiarity of some varieties of fruit to produce very different yields from year to year, for endogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvested product, before or after harvesting. This is of particular advantage, since it is thereby possible to achieve optimum adaptation to market requirements. Furthermore, growth regulators can at times improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, such as, for example, pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frosts.

Finally, the resistance of plants to frost, drought or a high salt content in the soil can be induced with growth regulators. Cultivation of plants in regions which are usually unsuitable for this purpose thereby becomes possible.

The active compounds can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface active agents, that is, emulsifying agents and- /or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water. By liquefied gaseous extenders or carriers are meant liquids which are gaseous at normal temperature and under atmospheric pressure, for example aerosol propellants, such as halogenated hydrocarbons as well as butane, propane, nitrogen and carbon dioxide. As solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products. As dispersing agents there are suitable: for example, lignin sulphite waste liquors and methylcellulose.

Adhesives such as carboxymethylcellulose and natural and synthetic polymers in the form of powders, granules or latices, such as gum arabic, polyvinylalcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and also as mixtures with fertilizers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are used as fungicides, the amount applied can be varied within a relatively wide range, depending upon the type of application. Thus the active compound concentrations in the use forms for the treatment of plant parts are generally between 1 and 0.0001% by weight, preferably between 0.5 and 0.001%. For seed treatment, active compound amounts of 0.001 to 50 g per kilogram of seed, preferably 0.01 to 10 g, are generally required. For the treatment of the soil, active compound concentrations of 0.00001 to 0.1% by weight, preferably 0.0001 to 0.02%, are required at the site of action.

When the compounds according to the invention are used as plant growth regulators, the amounts applied can be varied within a relatively wide range. In general, 0.01 to 50 kg, preferably 0.05 to 10 kg, of active compound are used per hectare of soil surface.

When the substances according to the invention are used as plant growth regulators, the rule is that they are applied within a preferred period of time, the exact definition of which depends on the climatic and vegetative circumstances.

The preparation and the use of the active compounds according to the invention can be seen from the examples below.

PREPARATION EXAMPLES

EXAMPLE 1

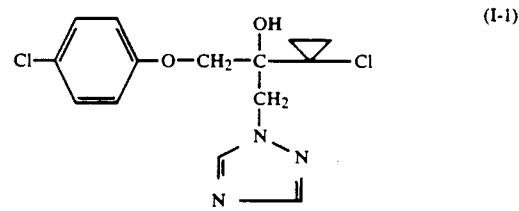
(I-1)

A solution 27.9 g (0.11 mol) of 2-(1-chlorocyclopropyl)-2-(4-chloro-phenoxymethyl)-oxirane in 50 ml of acetonitrile is added dropwise under a nitrogen atmosphere to a mixture of 29 g (0.42 mol) of 1,2,4-triazole, 19 g (0.14 mol) of potassium carbonate and 100 ml bf acetonitrile, and the reaction mixture is boiled under reflux. After completion of the addition, the mixture is heated for a further 8 hours under reflux. The mixture is then filtered off from the solid residue with suction and the filtrate is concentrated under reduced pressure. The remaining residue is taken up in ethyl acetate. The resultant solution is washed with water, dried over sodium sulphate and concentrated under reduced pressure. The product thus obtained is purified chromatographically through silica gel using chloroform/ethanol=97:3 as eluent. In this manner, 13.7 g (39% of theory) of 2-(1-chlorocyclopropyl)-1-(4-chlorophenoxy)-3-(1,2,4-triazol-1-yl)-propan-2-ol are obtained in the form of an oil.

$^1$H-NMR (80 MHz, CDCl$_3$): δ=0.5–1.4(m,4H), 4.1–4.4(m,3H), 4.75 (s,2H), 6.8–7.25 (m, 4H), 8.0 (s,1H), 8.17 (s, 1H).

Preparation of Starting Materials

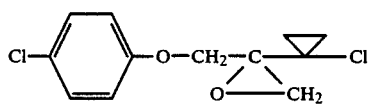 (II-1)

90 ml of absolute dimethyl sulphoxide are added dropwise at 10° C. under a nitrogen atmosphere and with stirring to a mixture of 3.9 g (0.13 mol) of sodium hydride (80% strength) and 27 g (0.12 mol) of trimethyloxosulphonium iodide. The mixture is stirred for a further hour at room temperature and then cooled to 10° C., and a solution of 27 g (0.11 mol) of 1-chlorocyclopropyl-4-chlorophenoxymethyl ketone in 40 ml of absolute dimethyl sulphoxide is added dropwise. The reaction mixture is initially stirred for 48 hours at 20° C., then warmed to 40° C. for 1 hour and then poured into water. The resulting mixture is extracted using ethyl acetate. The organic phase is washed with water, dried over sodium sulphate and concentrated under reduced pressure. In this manner, 27.9 g (98% of theory) of 2-(1-chlorocyclopropyl)-2-(4-chlorophenoxymethyl)-oxirane are obtained in the form of an oil.

$^1$H-NMR (60 MHz, CDCl$_3$): δ=0.75–1.4 (m, 4H), 2.8 (d, 1H), 3.05 (d, 1H), 4.25 (d, 1H), 4.58 (d, 1H), 6.8–7.4 (m, 4H).

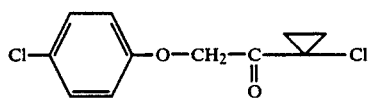 (VII-1)

49 g (0.38 mol) of 4-chlorophenol and 70 g (0.51 mol) of potassium carbonate are added successively to a solution of 51 g (0.33 mol) of 1-chloro-1-chloroacetyl-cyclopropane in 250 ml of acetonitrile. The mixture is heated for 8 hours under reflux, then filtered and concentrated by stripping off the solvent. The residue is taken up in ethyl acetate, and the solution is washed successively with dilute aqueous sodium hydroxide solution and water, dried over sodium sulphate and the solvent stripped off under reduced pressure. The residue is subjected to a distillation. In this manner, 27 g (33% of theory) of 1-chlorocyclopropyl-4-chlorophenoxymethyl ketone are obtained in the form of a liquid of boiling point 125°–127° C./0.1 mbar.

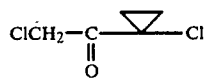 (X-1)

40.5 ml (0.5 mol) of sulphuryl chloride are slowly added dropwise at room temperature to a solution of 54 g (0.46 mol) of 1-acetyl-1-chloro-cyclopropane in 250 ml of methylene chloride. The mixture is initially stirred for 14 hours at room temperature and then for 30 minutes at 30° C. The reaction mixture is then successively washed with saturated aqueous sodium hydrogen carbonate solution and with water. The organic phase is then dried over sodium sulphate and concentrated under reduced pressure. In this manner, 51.5 g (74% of theory) of 1-chloro-1-chloroacetylcyclopropane are obtained in the form of an oily substance.

$^1$H-NMR (60 MHz, CDCl$_3$): δ=1.2–1.9 (m, 4H); 4.8 (s, 2H)

EXAMPLE 2

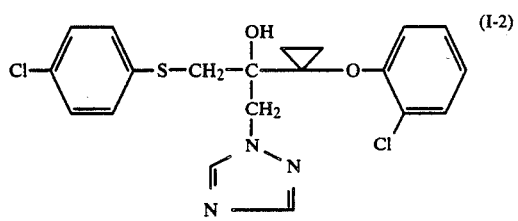 (I-2)

A mixture of 15 g (0.05 mol) of 2-[1-(2-chlorophenoxy)-cyclopropyl]-2-[(1,2,4-triazol-1-yl)-methyl]oxirane, 7.5 g (0.05 mol) of 4-chloro-thiophenol, 0.75 g (0.13 mol) of potassium hydroxide powder and 45 ml of acetonitrile is heated under reflux. The reaction mixture is filtered and the filtrate is concentrated by stripping off the solvent under reduced pressure. The product remaining in this process is subjected to a chromatographic purification. In this manner, 22 g (98% of theory) of 1-(4-chlorophenylmercapto)-2-[1-(2-chlorophenoxy)-cyclopropyl-3-(1,2,4-triazol-1-yl)-propan-2-ol are obtained in the form of an oily product.

$^1$H-NMR (80 MHz CDCl$_3$): δ=0.3–1.3 (m, 4H), 3.35 (d, 1H) 3.58 (d, 1H), 4.30 (s, 1H), 4.77 (s, 2H), 7.0–7.5 (m, 8H), 8.08 (s, 1H), 8.5 (s, 1H).

Preparation of the starting substances

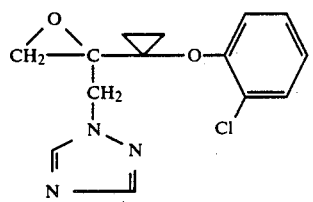 (IV-1)

135 ml of absolute dimethyl sulphoxide are added dropwise at 10° C. under a nitrogen atmosphere and with stirring to a mixture of 6 g (0.2 mol) of sodium hydride (80% strength) and 42 g (0.19 mol) of trimethyloxosulphonium iodide. The reaction mixture is stirred for 1 hour at room temperature and then cooled to 10° C., and a solution of 47 g (0.17 mol) of 1-(2-chlorophenoxy)-cyclopropyl-(1,2,4-triazol-1-yl)-methyl-ketone in 50 ml of absolute dimethyl sulphoxide is added dropwise. The mixture is stirred for a further 48 hours at room temperature and then warmed to 40° C. for 1 hour. The reaction mixture is then poured into water and extracted with with water and concentrated by stripping off the solvent under reduced pressure after drying over sodium sulphate. In this manner, 40.2 g (81% of theory) of 2-[1-(2-chlorophenoxy)-cyclopropyl]-2-[(1,2,4-triazol-1-yl)-methyl]oxirane are obtained in the form of an oily product.

$^1$H-NMR (60 MHz CDCl$_3$): δ=0.6–1.6 (m, 4H), 2.6 (d, 1H), 2.78 (d, 1H), 4.34 (d, 1H), 4.75 (d, 1H), 6.9–7.5 (m, 4H), 8.0 (s, 1H), 8.45 (s, 1H).

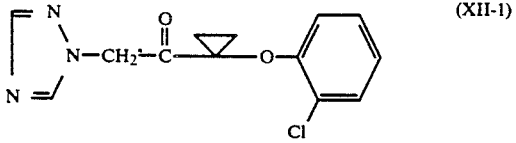 (XII-1)

A solution of 62 g (0.25 mol) of 1-chloroacetyl-1-(2-chlorophenoxy)-cyclopropane in 60 ml of acetonitrile is added dropwise to a mixture of 38.5 g (0.28 mol) of potassium carbonate, 58.4 g (0.85 mol) of 1,2,4-triazole and 140 ml of acetonitrile, and the reaction mixture is boiled under reflux. The reaction mixture is heated under reflux for a further 8 hours, then filtered and the mixture is concentrated by stripping off the solvent under reduced pressure. The residue remaining is taken up in ethyl acetate, washed with water, dried over sodium sulphate and the solvent then stripped off under reduced pressure. The remaining product is chromatographed on silica gel using chloroform/ethanol=99:1 as eluent. In this manner, 47 g (67% of theory) of 1-(2-chlorophenoxy)-cyclopropyl-(1,2,4-triazol-1-yl)-methyl ketone are obtained in the form of an oily product.

$^1$H-NMR (60 MHz, CDCl$_3$): δ=1.15-1.85 (m, 4H), 5.34 (s, 2H), 6.80-7.60 (m, 4H), 7.90 (s, 1H), 8.07 (s, 1H).

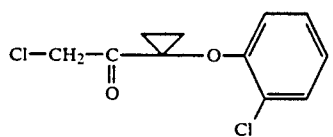 (X-2)

48 g (0.35 mol) of sulphuryl chloride are added dropwise at 20° C. with stirring and with cooling to a mixture of 61.7 g (0.29 mol) of 1-acetyl-1-(2-chlorophenoxy)-cyclopropane and 0.4 g of dibenzoyl peroxide. The reaction mixture is stirred for a further 4 hours at 20° C. and simultaneously irradiated using a 200 W light bulb. A mixture of ethyl acetate and toluene is then added to the reaction mixture. The mixture is washed with water, dried over sodium sulphate and concentrated by stripping off the solvent under reduced pressure. The remaining product is subjected to a vacuum distillation. In this manner, 62.3 g (87% of theory) of 1-chloroacetyl-1-(2-chlorophenoxy)-cyclopropane are obtained. Bp=117°-122° C./0.2 mbar

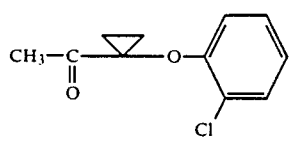 (XI-1)

A solution of 134 g (0.84 mol) of bromine in 130 ml of methylene chloride is added dropwise at 10° C. with stirring to a mixture of 100 g (0.83 mol) of 5-chloropentan-2-one and 400 ml of methylene chloride. After completion of the addition, the reaction mixture is stirred for a further 15 minutes and then poured into 500 ml of water. The organic phase is separated off, washed successively with 5% strength aqueous sodium carbonate solution and with water, then dried over sodium sulphate and concentrated by stripping off the solvent under reduced pressure. The residue is taken up in 200 ml of dimethylformamide, and the resulting solution is added dropwise at 60° C. to a mixture of 230 g of potassium carbonate, 106 g (0.83 mol) of 2-chlorophenol and 400 ml of dimethylformamide. The reaction mixture is initially stirred for 4 hours at 60° C. and then for 4 hours at 90° C. The mixture is then filtered from the solid residue with suction, the solvent is stripped off under reduced pressure and the remaining residue is taken up in a mixture of ethyl acetate and toluene. The organic phase is washed with water, dried over sodium sulphate and concentrated by stripping off the solvent under reduced pressure. The remaining residue is subjected to a vacuum distillation. In this manner, 92.5 g (53% of theory) of 1-acetyl-1-(2-chlorophenoxy)-cyclopropane are obtained in the form of a liquid of boiling point 81° C./0.2 mbar.

EXAMPLE 3

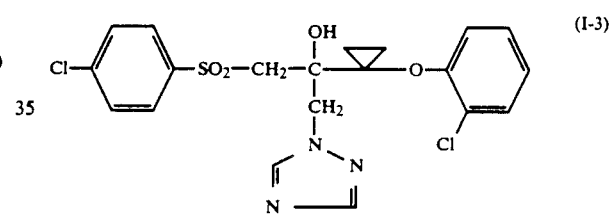 (I-3)

A solution of 10 g (23 mmol) of 1-(4-chlorophenylmercapto)-2-[1-(2-chlorophenoxy)-cyclopropyl]-3-(1,2,4-triazol-1-yl)-propan-2-ol in 50 ml of glacial acetic acid is heated to 80° C. and 20 ml of 35% strength hydrogen peroxide solution are added dropwise with stirring. The reaction mixture is warmed at 90° C. for a further 4 hours and then poured into water. The solid product is filtered off with suction and taken up in methylene chloride, and the solution is washed successively with dilute aqueous sodium hydroxide solution and water, dried over sodium sulphate and concentrated by stripping off the solvent under reduced pressure. In this manner, 60.4 g (69% of theory) of 1-(4-chlorophenylsulphonyl)-24-[1-(2-chlorophenoxy)-cyclopropyl]-3-(1,2,4 -triazol-1-yl)-propan-2-ol are obtained.

$^1$H-NMR (200 MHz, CDCl$_3$): δ=0.30-0.95 (m, 4H), 3.65 (d, 1H), 3.87 (d, 1H), 4.85 (d, 1H), 5.11 (d, 1H), 7.0-7.4 (m, 4H), 7.55 (d, 2H), 7.80 (d, 2H), 8.0 (s, 1H), 8.44 (s, 1H).

The compounds, which are shown by formula in the following Table 2, are prepared according to the methods which are mentioned in Examples 1 to 3 and in the description.

TABLE 2
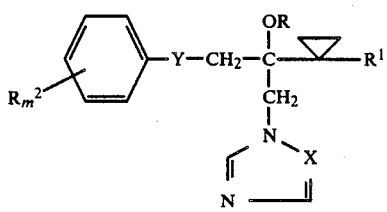
| Example No. | Compound No. | $R_m^2$ | R | $R^1$ | Y | X | Melting point (°C.) |
|---|---|---|---|---|---|---|---|
| 4 | I-4 | 4-F | H | Cl | O | N | * |
| 5 | I-5 | 2,4-Cl$_2$ | H | ◯ phenyl | O | N | 123 |
| 6 | I-6 | 2-CH$_3$, 4-Cl | H | ◯ phenyl | O | N | 125 |
| 7 | I-7 | 4-CH=N—OCH$_3$ | H | ◯ phenyl | O | N | 88 |
| 8 | I-8 | 4-Cl | H | ◯ phenyl | O | N | 140 |
| 9 | I-9 | 4-Cl | H | ◯-Cl | O | N | resin |
| 10 | I-10 | 2,4-Cl$_2$ | H | ◯-Cl | O | N | resin |
| 11 | I-11 | 4-OCF$_3$ | H | ◯-Cl | O | N | resin |
| 12 | I-12 | 2-CH$_3$, 4-Cl | H | ◯-Cl | O | N | 140 |
| 13 | I-13 | 4-CH=N—OCH$_3$ | H | ◯-Cl | O | N | 113 |
| 14 | I-14 | 4-F | H | ◯ phenyl | O | N | 142 |
| 15 | I-15 | CF$_3$ | H | ◯ phenyl | O | N | 158 |

TABLE 2-continued

[Structure: Rm²-phenyl-Y-CH₂-C(OR)(CH₂-N=N-X=)-cyclopropyl-R¹]

| Example No. | Compound No. | Rm² | R | R¹ | Y | X | Melting point (°C.) |
|---|---|---|---|---|---|---|---|
| 16 | I-16 | 4-CH₃ | H | phenyl | O | N | 137 |
| 17 | I-17 | 4-OCF₃ | H | phenyl | O | N | 148 |
| 18 | I-18 | 4-CF₃ | H | 4-Cl-phenyl | O | N | 127 |
| 19 | I-19 | 4-CH₃ | H | 4-Cl-phenyl | O | N | resin |
| 20 | I-20 | 2-Cl | H | 4-Cl-phenyl | O | N | resin |
| 21 | I-21 | 4-F | H | 4-Cl-phenyl | O | N | 124 |
| 22 | I-22 | 2-Cl | H | phenyl | O | N | 136 |
| 23 | I-23 | 2-CH₃, 4-Cl | H | 2,4-di-Cl-phenyl | O | N | resin |
| 24 | I-24 | 4-Cl | H | 2,4-di-Cl-phenyl | O | N | 118 |
| 25 | I-25 | 4-CH=N—OCH₃ | H | 2,4-di-Cl-phenyl | O | N | resin |

TABLE 2-continued

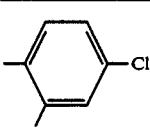

| Example No. | Compound No. | $R_m^2$ | R | $R^1$ | Y | X | Melting point (°C.) |
|---|---|---|---|---|---|---|---|
| 26 | I-26 | 2,4-Cl$_2$ | H | 3,4-Cl$_2$-C$_6$H$_3$ | O | N | resin |
| 27 | I-27 | 2-Cl, 4-OCF$_3$ | H | 4-Cl-C$_6$H$_4$ | O | N | 113 |
| 28 | I-28 | 4-OCF$_3$ | H | 3,4-Cl$_2$-C$_6$H$_3$ | O | N | 85 |
| 29 | I-29 | 4-Cl | H | C$_6$H$_5$ | S | N | 108 |

*The compound disclosed in Example 4 is characterized by its $^1$H-NMR spectrum (560 MHz, CDCl$_3$):
δ = 0.55–0.70 (m, 2H), 0.80–0.95 (m, 1H), 1.10–1.20 (m, 1H), 4.10 (s, 1H), 4.16 (d, 1H), 4.30 (d, 1H), 4.75 (d, 1H), 4.80 (d, 1H), 6.80–7.05 (m, 4H), 8.02 (s, 1H), 8.30 (s, 1H).

The compound of the formula given below is employed as the comparison substance in the following used examples:

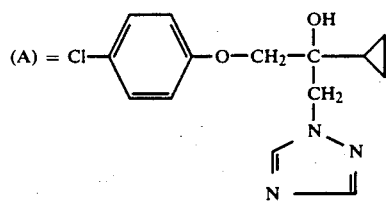

(known from EP-OS (European Published Specification) No. 0,040,345).

Example A

Sphaerotheca test (cucumber)/protective
Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, the compound of the formula (I-1) according to the invention shows a clearly better action than the comparison substance (A).

Example B

*Leptosphaeria nodorum* test D (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabin at 20° C. and 100% relative atmospheric humidity.

The plants are placed in a greenhouse at a temperature of about 15° C. and a relative atmospheric humidity of about 80%.

Evaluation is effected 10 days after the inoculation. 0% means a degree of action which corresponds to that of the untreated control, whereas a degree of action of 100% means that no infestation is present.

In this test, the compound (I-1) according to the invention shows a clearly better action than the comparison substance (A).

Example C

Growth of soy beans
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Soy bean plants are grown in a greenhouse until the first secondary leaf has unfolded completely. In this stage, the plants are sprayed with the preparations of active compound until dripping wet. After two weeks, the additional growth is measured on all the plants and the growth is calculated in percent of the additional growth of the control plants. 100% growth denotes growth corresponding to that of the control plants, and 0% denotes cessation of growth. Values above 100% indicate promotion of growth, whereas values below 100% indicate inhibition of growth.

In this test, the compound (I-1) according to the invention shows a very good growth-inhibiting action.

Example D

Growth of cotton
Solvent: 30 parts by weight of dimethylformamide
Emulsifier: 1 part by weight of polyoxyethylene sorbitan monolaurate To produce a suitable preparation of active compound, 1 part by weight of active compound is mixed with the stated amounts of solvent and emulsifier and the mixture is made up to the desired concentration with water.

Cotton plants are grown in a greenhouse until the fifth secondary leaf has unfolded completely. At this stage, the plants are sprayed with the preparations of active compound until dripping wet. After two weeks, the additional growth of all the plants is measured and the growth is calculated in per cent of the additional growth of the control plants. 100% growth denotes growth corresponding to that of the control plants and 0% denotes cessation of growth. Values above 100% indicate promotion of growth, whereas values below 100% indicate inhibition of growth.

In this test, the compound (I-1) according to the invention shows a very good growth-inhibiting action.

It will be appreciated that the instant specification and claims are set forth by way of illustration and not limitation, and that various modifications and changes may be made without departing from the spirit and scope of the present invention.

What is claimed is:

1. A hydroxyethyl-triazolyl derivative or addition product thereof with an acid or metal salt, of the formula

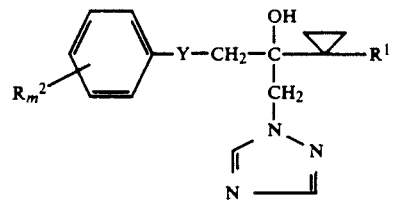

in which
$R^1$ represents fluorine, chlorine, phenyl which is optionally mono- or disubstituted by chlorine, or the grouping —O——$R^3$, wherein
$R^3$ is phenyl which is optionally mono- or disubstituted by chlorine,
$R^2$ represents fluorine, chlorine, methyl, trifluoromethyl, trifluoromethoxy, trifluromethylthio, methoximinomethyl or phenyl,
m represent the numbers 1 or 2, and
Y represents oxygen or $SO_2$.

2. A compound according to claim 1, wherein such compound is 2-(1-chlorocyclopropyl)-1-(4-chlorophenoxy)-3-(1,2,4-triazol-1-yl)-propan-2-ol of the formula

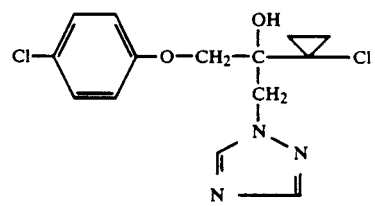

or an addition product thereof with an acid or metal salt.

3. A compound according to claim 1, wherein such compound is 1-(4-chlorophenylsulphonyl)-2-[1-(2-chlorophenoxyl)-cyclopropyl]-3-(1,2,4-triazol-1-yl)-propan-2-ol of the formula

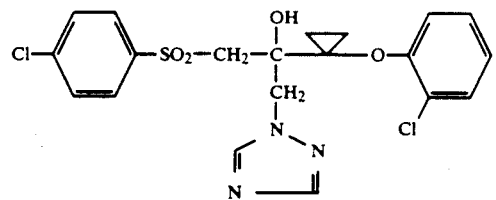

or an addition product thereof with an acid or metal salt.

4. A compound according to claim 1, wherein such compound is 2-(1-chlorocyclopropyl)-1-(4-fluorophenoxy)-3-(1,2,4-triazol-1-yl)-propan-2-ol of the formula

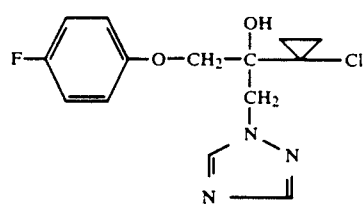

or an addition product thereof with an acid or metal salt.

5. A compound according to claim 1, wherein such compound is 2-(1-phenyl-cyclopropyl)-1-(2,4-dichloro-phenoxy)-3-(1,2,4-triazol-1-yl)-propan-2-ol of the formula

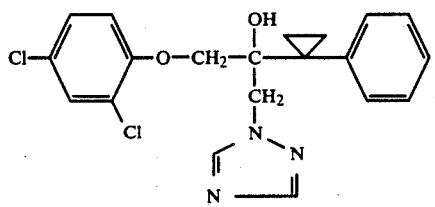

or an addition product thereof with an acid or metal salt.

6. A fungicidal or plant growth regulating composition comprising a fungicidal or plant growth regulating effective amount of a compound or addition product according to claim 1 and an inert diluent.

7. A method of combating fungi which comprises applying to such fungi or to a fungus habitat a fungicidal or plant growth regulating effective amount of a compound or addition product according to claim 1.

8. The method according to claim 7, wherein such compound is
2-(1-chlorocyclopropyl)-1-(4-chlorophenoxyl)-3-(1,2,4-triazol-1-yl)-propan-2-ol,
1-(4-chlorophenylsuylphonyl)-2-[1-(2-chlorophenoxyl)-cyclopropyl]-3-(1,2,4-triazol-1-yl)-propan-2-ol,
2-(1-chlorocyclopropyl)-1-(4-flurophenoxy)-3-(1,2,4-triazol-1-yl)-propan-2-ol, or
2-(1-phenyl-cyclopropyl)-1-(2,4-dichloro-phenoxy)-3-(1,2,4-triazol-1-yl)-propan-2-ol,
or an addition product thereof with an acid or metal salt.

9. A method of regulating the growth of plants which comprises applying to such plants or to a locus in which such plants are growing or are to be grown a plant growth regulating effective amount of a compound or addition product according to claim 1.

* * * * *